US011642457B2

(12) United States Patent
Yigal et al.

(10) Patent No.: US 11,642,457 B2
(45) Date of Patent: May 9, 2023

(54) INJECTOR SELF-TEST AND INJECTOR DOOR UNLOCKING MECHANISM RESPONSIVE THERETO

(71) Applicant: West Pharma. Services IL, Ltd., Ra'anana (IL)

(72) Inventors: Gil Yigal, Gan Yavne (IL); Yossi Bar-El, Beit Arye (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 261 days.

(21) Appl. No.: 16/637,043

(22) PCT Filed: Aug. 2, 2018

(86) PCT No.: PCT/US2018/045004
§ 371 (c)(1),
(2) Date: Feb. 6, 2020

(87) PCT Pub. No.: WO2019/032375
PCT Pub. Date: Feb. 14, 2019

(65) Prior Publication Data
US 2020/0238003 A1 Jul. 30, 2020

Related U.S. Application Data

(60) Provisional application No. 62/543,701, filed on Aug. 10, 2017.

(51) Int. Cl.
*A61M 5/145* (2006.01)
*A61M 5/142* (2006.01)

(52) U.S. Cl.
CPC .... *A61M 5/14566* (2013.01); *A61M 5/14248* (2013.01); *A61M 2205/3306* (2013.01); *A61M 2205/70* (2013.01)

(58) Field of Classification Search
CPC ................ A61M 5/24; A61M 5/14566; A61M 5/24248; A61M 5/1456; A61M 2005/2414; A61M 2005/2496
See application file for complete search history.

(56) References Cited

U.S. PATENT DOCUMENTS 6,740,059 B2 * 5/2004 Flaherty ............ A61M 5/14248
604/67
9,610,404 B2 4/2017 Rotstein
(Continued)

FOREIGN PATENT DOCUMENTS

EP 2932993 A1 10/2015
EP 3031486 A1 * 6/2016
(Continued)

OTHER PUBLICATIONS

Int'l Preliminary Report on Patentability dated Feb. 11, 2020 in Int'l Application No. PCT/US2018/045004.
(Continued)

*Primary Examiner* — Laura A Bouchelle
(74) *Attorney, Agent, or Firm* — Blank Rome LLP (57) ABSTRACT

An injector is configured to receive therein a cartridge containing a substance to be dispensed. The injector includes an injector housing and an injector door movably mounted to the injector housing between a fully closed position and a fully open position. The injector door is initially locked in an at least partially closed position preventing insertion of the cartridge into the injector. The injector further includes a controller configured to conduct an initial self-test on operability of at least one component of the injector. The self-test has a single pass or fail outcome, wherein the injector door is unlocked and enabled to be moved into the
(Continued)

fully open position, to enable insertion of the cartridge into the injector, solely upon achievement of the self-test pass outcome.

30 Claims, 6 Drawing Sheets

(56) References Cited

U.S. PATENT DOCUMENTS

| | | |
|---|---|---|
| 2009/0216194 A1 | 8/2009 | Elgaard et al. |
| 2013/0310753 A1 | 11/2013 | Cabiri |
| 2014/0188073 A1 | 7/2014 | Cabiri et al. |
| 2016/0346478 A1 | 12/2016 | Bar-El et al. |
| 2017/0043092 A1* | 2/2017 | Murakami ............. A61M 5/20 |
| 2018/0154081 A1 | 6/2018 | Bar-El et al. |
| 2020/0114068 A1* | 4/2020 | Schmidlin ........... A61M 5/1454 |

FOREIGN PATENT DOCUMENTS

| | | |
|---|---|---|
| JP | 2012501771 A | 1/2012 |
| JP | 201250847 A | 3/2012 |
| JP | 2014516702 A | 7/2014 |
| KR | 20140000766 U | 2/2014 |
| WO | 2005077441 A2 | 8/2005 |
| WO | 2014052676 A1 | 4/2014 |

OTHER PUBLICATIONS

Int'l Search Report and Written Opinion dated Jan. 4, 2019 in Int'l Application No. PCT/US2018/045004.
Office Action dated Jul. 14, 2020 in Japanese Application No. 2020-507099.

\* cited by examiner

INJECTOR SELF-TEST AND INJECTOR DOOR UNLOCKING MECHANISM RESPONSIVE THERETO

CROSS-REFERENCE TO RELATED APPLICATIONS

This application is a Section 371 of International Application No. PCT/US2018/045004, filed Aug. 2, 2018, which was published in the English language on Feb. 14, 2019, under International Publication No. WO 2019/032375 A1, which claims the benefit of priority under 35 U.S.C. § 119(e) to U.S. Provisional Patent Application No. 62/543,701, titled "Injector Self-Test and Injector Door Unlocking Mechanism Responsive Thereto", filed on Aug. 10, 2017, the entire contents of each of which are incorporated herein by reference in their entirety.

BACKGROUND OF THE DISCLOSURE

The present disclosure is generally directed to a cartridge loaded injector, and, more particularly, to a cartridge loaded injector configured to conduct an initial self-test prior to unlocking a door thereof for cartridge loading.

An injector, such as, for example, a drug injector, is typically loaded with a cartridge containing therein a substance, e.g., a medicament or drug, to be dispensed. The cartridge may be pre-loaded prior to delivery to a user, or, alternatively, the cartridge may be loaded by the user prior to use. Malfunction of an injector after insertion of the cartridge may result in waste of the cartridge, the wasted substance therein being both valuable and expensive. This may occur, for example, because a cartridge is generally unsealed during loading into the injector to place the substance within the cartridge in fluid communication with an injection needle of the injector.

Some conventional injectors conduct a self-check of the device to test whether the device is fully operational, and employ a status check indicator that indicates whether the device has passed the check. A user is instructed not to insert the cartridge into the injector until the check indicator indicates a successful self-check. Merely instructing a user to wait for a positive device check before loading the cartridge into the injector, however, makes the injector use more complicated and leaves potential for possible user errors nonetheless. Other conventional injectors employ a drainage port to recover the substance from the inserted cartridge should the injector malfunction. Recovery of the substance via a drainage port, however, may also result in multiple problems, such as, for example, substance contamination.

Therefore, it would be advantageous to manufacture an injector generally configured to reduce the number of user performed steps required to prepare the injector for use. It would also be advantageous to maintain the door thereof in a closed, locked configuration until the injector performs and passes a self-test, to prevent insertion of the cartridge into a faulty injector.

BRIEF SUMMARY OF THE DISCLOSURE

Briefly stated, one aspect of the present disclosure is directed to an injector configured to receive therein a cartridge containing a substance to be dispensed. The injector includes an injector housing and an injector door movably mounted to the injector housing between a fully closed position and a fully open position. The injector door is initially locked in an at least partially closed position preventing insertion of the cartridge into the injector. The injector further includes a controller configured to conduct an initial self-test on operability of at least one component of the injector. The self-test has a single pass or fail outcome, wherein the injector door is unlocked and enabled to be moved into the fully open position, to enable insertion of the cartridge into the injector, solely upon achievement of the self-test pass outcome.

Another aspect of the present disclosure is directed to a method of operation of an injector configured to receive therein a cartridge containing a substance to be dispensed. The method includes the steps of: conducting, via a controller of the injector, an initial self-test on operability of at least one injector component, the self-test having a single pass or fail outcome; and unlocking an injector door solely upon achievement of the self-test pass outcome, the injector door being movably mounted to a housing of the injector between a fully closed position and a fully open position, the injector door being previously locked in an at least partially closed position preventing insertion of the cartridge into the injector.

BRIEF DESCRIPTION OF THE DRAWINGS

The following detailed description of aspects of the disclosure will be better understood when read in conjunction with the appended drawings. It should be understood, however, that the invention is not limited to the precise arrangements and instrumentalities shown. In the drawings.

DETAILED DESCRIPTION OF THE DISCLOSURE

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the injector, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-5 an injector, generally designated 10, in accordance with an embodiment of the present disclosure. In the illustrated embodiment, the injector 10 takes the form of a wearable injector (patch injector), such as, for example, without limitation, a wearable drug injector, but the disclosure is not so limited. The injector 10 may be deliverable to a user in a packaging 50 (FIG. 1), as will be discussed in further detail below.

As should be understood by those of ordinary skill in the art, the injector 10 generally includes a housing 12 having a first surface 14 configured to contact a skin surface of a user (not shown), e.g., a patient, the first surface 14 having an opening 14a therein. In the illustrated embodiment, the first surface 14 defines a base surface of the injector housing 12, but the disclosure is not so limited. The housing 12 also includes a second surface 16 opposing the first surface 14. In the illustrated embodiment, the second surface 16 defines a top, external surface of the injector housing 12, but the disclosure is not so limited. As also should be understood by those of ordinary skill in the art, an injection needle (not shown) is movably mounted within the injector housing 12 and is translatable between a retracted position (not shown), wherein at least a tip of the injection needle is contained within the injector housing 12, and an injection position (not shown), wherein at least the tip of the injection needle protrudes from the injector housing 12 through the opening 14a and into the skin of a user (not shown).

Figure 4:
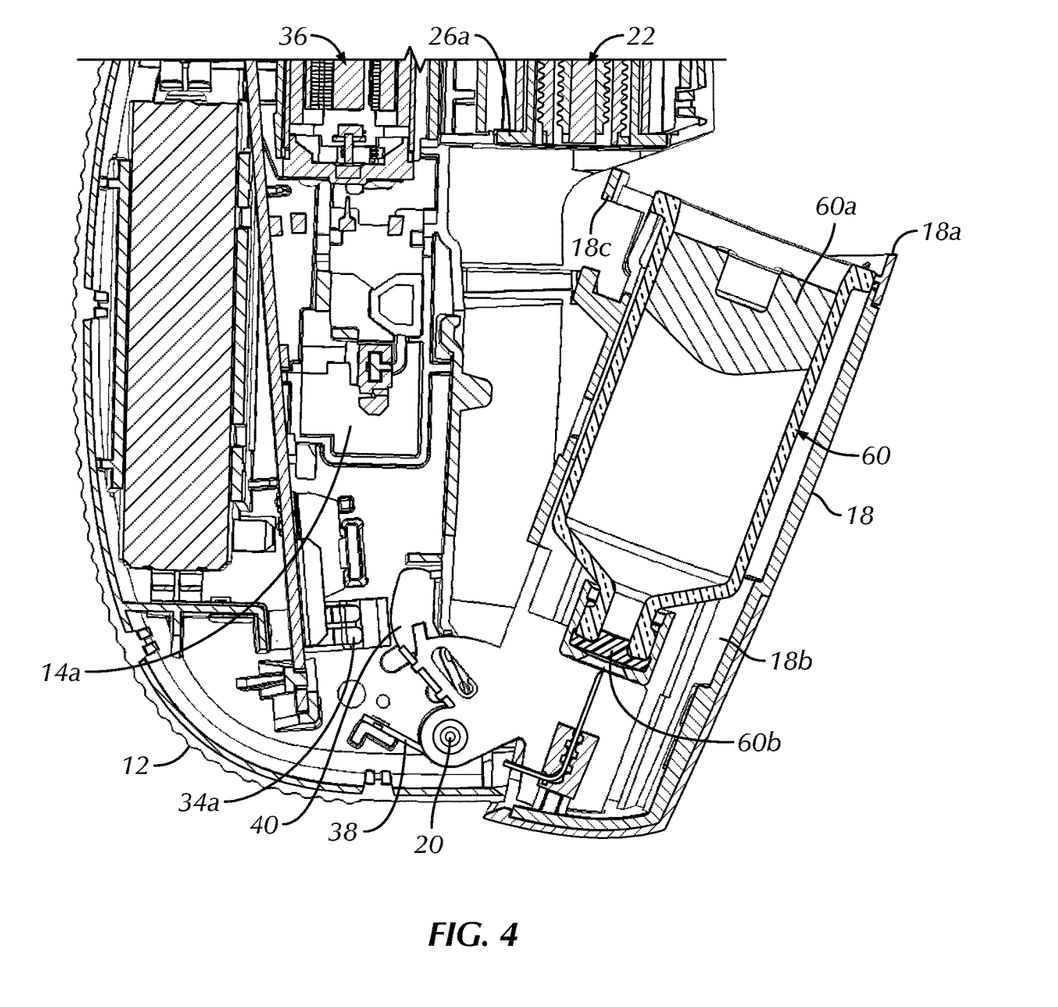
FIG. 4 is a cross-sectional view of the injector of FIG. 1, taken along the sectional line 2-2 of FIG. 1, with the movable locking member retracted out of the pathway of the cartridge door and the cartridge door being positioned in a fully open position thereof and a cartridge loaded into the cartridge door.
Figure 5:
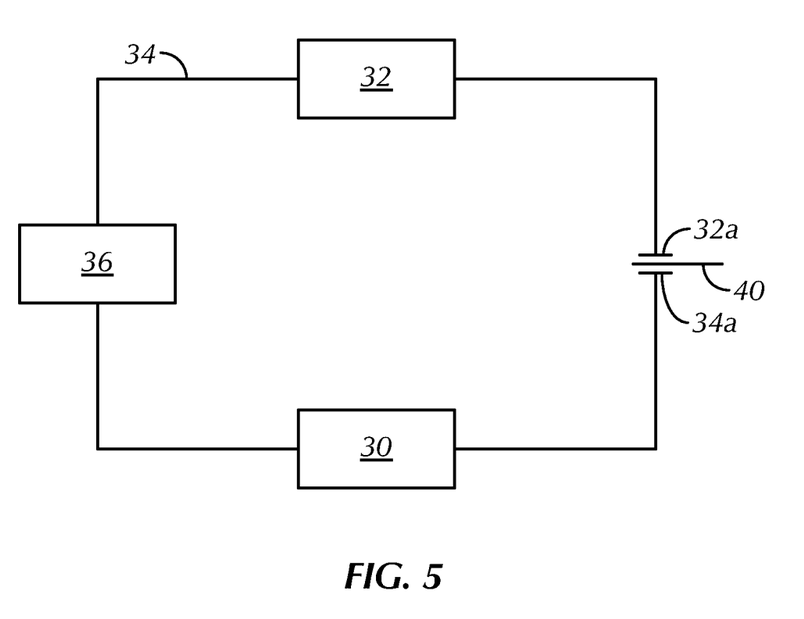
FIG. 5 is a schematic illustration of a power supply circuit of the injector of FIG. 1, having an electrically insulated member interposed between at least one contact of a power supply and a respective at least one opposing contact of the power supply circuit.

The injector 10 is configured to receive therein a sealed cartridge 60 (FIG. 4) containing a substance (not shown), e.g., medicament. The cartridge 60 is sealed at one end by a piston 60a and at another end by a pierceable septum 60b. After (or during) insertion of the cartridge 60 into the injector 10, the cartridge 60 is unsealed and fluidly connected to the injection needle, in a manner well understood by those of ordinary skill in the art (via piercing of the septum 60b), to dispense the substance within the cartridge 60 through the injection needle to a user. An injector door 18 is movably mounted to the injector housing 12 between a fully closed position (FIGS. 1-2B) and a fully open position (FIG. 4). The injector door 18 is openable to receive the cartridge 60 within the injector 10. In the illustrated embodiment, the injector door 18 takes the form of a cartridge door, but the disclosure is not so limited. The cartridge door 18 includes an open end 18a for receiving, e.g., slidably, the cartridge 60 therethrough, and an interior channel 18b to receive the cartridge 60 therein. The interior channel 18b may be sized and shaped to receive and stabilize the cartridge 60 therein. Alternatively, the interior channel 18b may include a cartridge cradle, a cartridge track, individual stabilizing members, combinations thereof, or the like (not shown) to receive and stabilize the cartridge 60 in the interior channel 18b.

In an at least partially closed position of the cartridge door 18 (FIG. 3), the interior channel 18b is not sufficiently accessible from outside of the injector housing 12 to insert a cartridge 60 therein. For example, in the illustrated embodiment, the open end 18a of the cartridge door 18 is sufficiently obscured/covered by a portion of the injector housing 12 such that access to the interior channel 18b is prevented and the cartridge 60, therefore, cannot be inserted into the interior channel 18b. In the fully open position of the cartridge door 18 (FIG. 4), the open end 18a of the cartridge door 18 is sufficiently exposed/uncovered to permit insertion of the cartridge 18 therethrough and into the interior channel 18b.

In the illustrated embodiment, the cartridge door 18 is pivotably attached to the injector housing 12, e.g., via pin connection 20, proximate a closed, distal end of the interior channel 18b, opposite the open end 18a, but the disclosure is not so limited. As shown best in FIGS. 1 and 2A, the cartridge door 18 is substantially flush with the exterior body of the injector housing 12 in the fully closed position. As shown in FIG. 4, the cartridge door 18 is pivoted away from the injector housing 12 in the open position, whereby the interior channel 18b is accessible from the open end 18a of the cartridge door 18. Other non-limiting examples of a cartridge door 18 movably mounted to an injector housing 12 are described in U.S. Patent Application Publication No. 2018/0154081, entitled, "Cartridge Insertion For Drug Delivery Device," the entire contents of which are incorporated by reference herein.

A biasing member 38 may be mounted in the injector housing 12 and configured to bias the cartridge door 18 into the fully open position thereof. In the illustrated embodiment, the biasing member 38 takes the form of a torsion spring mounted between a non-movable member of the injector housing 12 and a member of the movable cartridge door 18, i.e., the torsion spring 38 abuts the injector housing 12 at one end thereof and abuts the cartridge door 18 at an opposing end thereof. In the closed position of the cartridge door 18, the torsion spring 38 is at least partially compressed, storing potential energy proportional to the amount of twisting thereof. When the torsion spring 38 is uninhibited (as will be described in further detail below), the torsion spring 38 expands, i.e., untwists, to move the cartridge door 18 toward the fully open position thereof. In the illustrated embodiment, the helical center of the torsion spring 38 is mounted around the pin connection 20, but may be otherwise positioned. As also should be understood by those of ordinary skill in the art, the biasing member 38 may alternatively take the form of other members capable of storing and releasing energy. Non-limiting examples include other springs (e.g., coil or leaf springs) and the like. Alternatively, a biasing member 38 may not be employed in the injector 10 and the cartridge door 18 may be manually movable to the open position thereof.

The injector 10 further includes a driving assembly 22 (FIGS. 2A, 3 and 4) positioned and configured to engage and advance the piston 60a through the cartridge 60, to, in turn, expel the substance out of the cartridge 60. In one non-limiting example, the driving assembly 22 may include a plurality of threaded shafts threadably connected to one another in a telescopic manner whereby rotation of at least one of the shafts linearly translates at least another of the shafts, i.e., a telescopic driving assembly, but the disclosure is not so limited. As shown, for example, the driving assembly 22 includes a first shaft 24 and a second shaft 26 telescopically connected with the first shaft 24 and axially movable relative to the first shaft 24. Rotation of the first shaft 24 axially drives the second shaft 26 from a retracted configuration (FIG. 4) to axially extend, engage and advance the piston 60a through the cartridge 60. In the retracted configuration, the driving assembly 22 is withdrawn from the interior channel 18b of the cartridge door 18 and does not interfere with movement of the cartridge door 18 between the fully closed and the fully open positions thereof. As the driving assembly 22 begins to axially extend, the second shaft 26 extends into the interior channel 18b.

In the illustrated embodiment, an optional third shaft 28 is threadedly connected to the first shaft 24 and threadedly connected to the second shaft 26, thereby connecting the first shaft 24 with the second shaft 26. Thus, rotation of the first shaft 24 rotates and axially drives the third shaft 28, which, in turn, axially drives the second shaft 26. The second shaft 26 is, therefore, axially movable relative to the first shaft 24 and the third shaft 28. Accordingly, the first, third and second shafts 24, 26, 28 form an axially telescoping driving assembly. Other non-limiting examples of telescoping driving assemblies are described in U.S. Patent Application Publication No. 2016/0346478, entitled "Linear Rotation Stabilizer For A Telescoping Syringe Stopper Driverdriving Assembly", the entire contents of which are incorporated by reference herein.

As should be understood by those of ordinary skill in the art, the injector 10 further comprises a controller 30 (shown schematically in FIG. 5), e.g., a processor, that directs operation of the injector 10 and a power supply 32 to power the controller 30 and other power-operated components of the injector 10. In the illustrated embodiment, the power supply 32 takes the form of a battery, but the disclosure is not so limited. A power supply circuit 34 (shown schematically in FIG. 5) electrically connects the battery 32 with the controller 30 and the other power-operated components of the injector 10. For example, the power supply circuit 34 may also connect the battery 32 with an actuator 36. Non-limiting examples of an actuator 36 include a motor, a spring actuator, a gaseous actuator, a chemical actuator, an electrical actuator, an electromechanical actuator, combinations thereof, or the like. Upon activation of the actuator 36 by the controller 30 (in a manner well understood by those of ordinary skill in the art), the actuator 36 is configured to drive the driving assembly 22 (in a manner well understood by those of ordinary skill in the art), e.g., via a series of interconnected rotatable gears 36a, 23, 22a (FIGS. 2A, 3), from an initial position, unengaged with the cartridge 60, into engagement with the cartridge 60 (in a manner well understood by those of ordinary skill in the art and as will be generally explained below).

Prior to use of the injector 10, the controller 30 is configured to conduct an initial self-test on operability of at least one component of the injector 10 to determine whether the injector 10 is properly functioning and ready for use or whether the injector 10 is malfunctioning, i.e., whether any of the at least one component tested is not properly functioning. The controller 30 may be programmed to conduct the self-test upon powering on. Alternatively, the self-test may be user-activated, via the injector 10 itself or remotely. Non-exhaustive examples of operative components of the injector 10 that may be tested may include, sensors (not shown), e.g., optical sensors, configured to detect motion of movable components of the injector 10, the actuator 36, the power supply 32, the driving assembly 32, other functions of the controller 30 and the like. The self-test has a single "pass" or "fail" outcome. That is, all components of the injector 10 that are tested during the self-test must be properly functioning for the self-test to achieve a "pass" outcome. Otherwise, if any component of the injector 10 that is tested during the self-test is not properly functioning, then the self-test will achieve a "fail" outcome.

The cartridge door 18 is initially locked in an at least partially closed position (FIG. 3), preventing insertion of the cartridge 60 into the injector 10, until the self-test is completed and with a "pass" outcome. That is, a movable locking mechanism protrudes into a pathway of the cartridge door 18 from the fully closed position thereof to the fully open position thereof, blocking the cartridge door 18 from being able to reach the fully open position thereof. The movable locking mechanism is configured to be withdrawn from the pathway of the cartridge door 18 solely upon achievement of the self-test "pass" outcome. The cartridge door 18 is, thereafter, unlocked and enabled to move into the fully open position thereof, to enable insertion of the cartridge 18 into the injector 10.

Advantageously, the locking mechanism preserves the integrity of an unused, sealed cartridge 60, as the cartridge 60 cannot be inserted into the injector 10 (and subsequently unsealed), unless the injector 10 passes the self-test, and, therefore, is confirmed to be a properly functioning injector 10. If any of the components tested by the self-test trigger a "fail" self-test outcome, the locking mechanism will not be withdrawn from the pathway of the cartridge door 18, thereby preventing a user from inserting and wasting a cartridge 60 into a malfunctioning injector 10.

In the illustrated embodiment, the driving assembly 22 operates as the movable locking mechanism, but the disclosure is not so limited. As shown best in FIG. 2A, the driving assembly 22 is axially aligned with the interior channel 18b of the cartridge door 18 when the cartridge door 18 is oriented in the fully closed position thereof. As shown in FIG. 3, the driving assembly 22 is initially positioned, i.e., prior to achievement of the self-test "pass" outcome, in a partially extended state, such that at least a distal portion 26a of the second shaft 26 extends into the interior channel 18b of the cartridge door 18. Accordingly, the second shaft 26 blocks the cartridge door 18 from moving into the fully open position thereof. As one example, a projection 18c from the cartridge door 18 proximate the open end 18a makes contact with the distal end 26a of the second shaft 26 during movement of the cartridge door 18 from the fully closed position thereof to the fully open position thereof, thereby blocking the cartridge door 18 from further movement toward the fully open position thereof. The driving assembly 22 is withdrawn into the retracted configured thereof (see FIG. 4) solely when the self-test achieves a "pass" outcome, i.e., the actuator 36 drives the driving assembly 22 in a reverse rotational direction from the rotational direction that extends the driving assembly 22. In the retracted configuration thereof, the driving assembly 22 is withdrawn from the pathway of the cartridge door 18.

In one embodiment, an electrically insulated member 40 may be initially positioned in a first state (FIGS. 2A, 2B and schematically in FIG. 5), whereat the electrically insulated member 40 is interposed between at least one contact 32a (positive or negative) of the power supply 32 and a respective at least one opposing contact 34a of the power supply circuit 34 (of opposite charge from the power supply contact 32a), thereby electrically disconnecting the power supply 32 from the power supply circuit 34 (such that no power is provided to the controller 30 and other injector components) to prevent drainage of the power supply 32 prior to injector 10 use. The electrically insulated member 40 is movable to a second state (FIGS. 3, 4), whereat the electrically insulated member 40 is removed from between the at least one contact 32a of the power supply 32 and the respective at least one opposing contact 34a of the power supply circuit 34, thereby electrically connecting the power supply 32 with the power supply circuit 34 and providing power to the injector components, including the controller 30.

In the illustrated embodiment, as shown in FIGS. 2A-4, the electrically insulated member 40 takes the form of polymeric arm coupled to the cartridge door 18. As should be understood however, the electrically insulated member 40 may be constructed of alternative electrically insulating materials currently known or that later become known. The arm 40 may be fixedly coupled with the cartridge door 18 in a manner well understood by those of ordinary skill in the art. That is, the arm 40 moves, e.g., pivots, along with movement, e.g., pivoting, of the cartridge door 18. Alternatively, the arm 40 may be integrally formed, i.e., unitary and monolithic, with the cartridge door 18.

Figure 1:
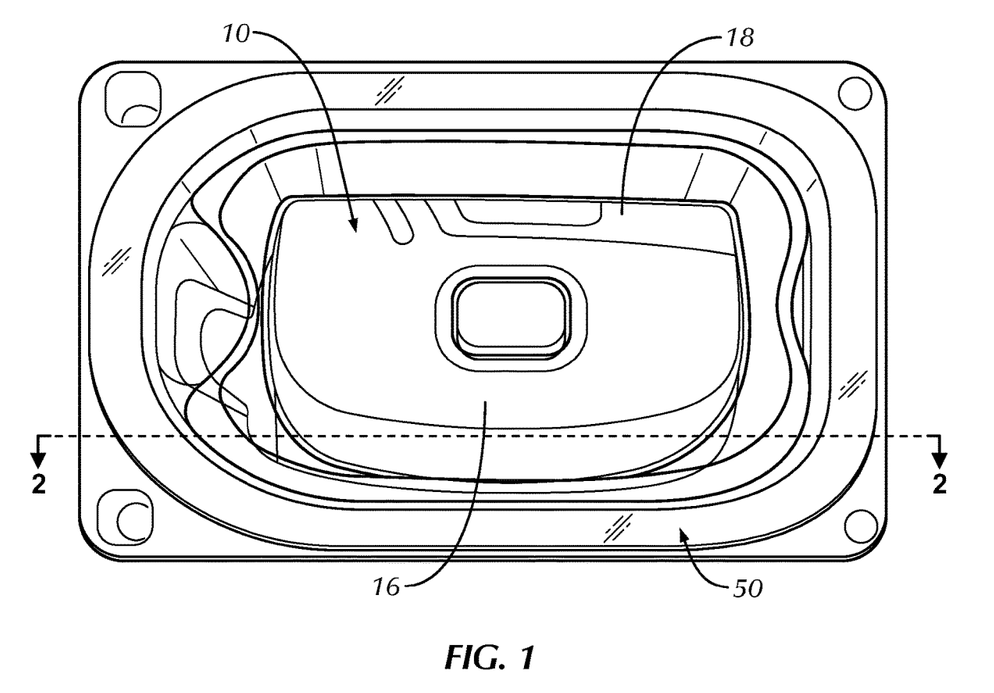
FIG. 1 is a top perspective view of a wearable injector placed in a packaging thereof, in accordance with an embodiment of the present disclosure.
Figure 2A:
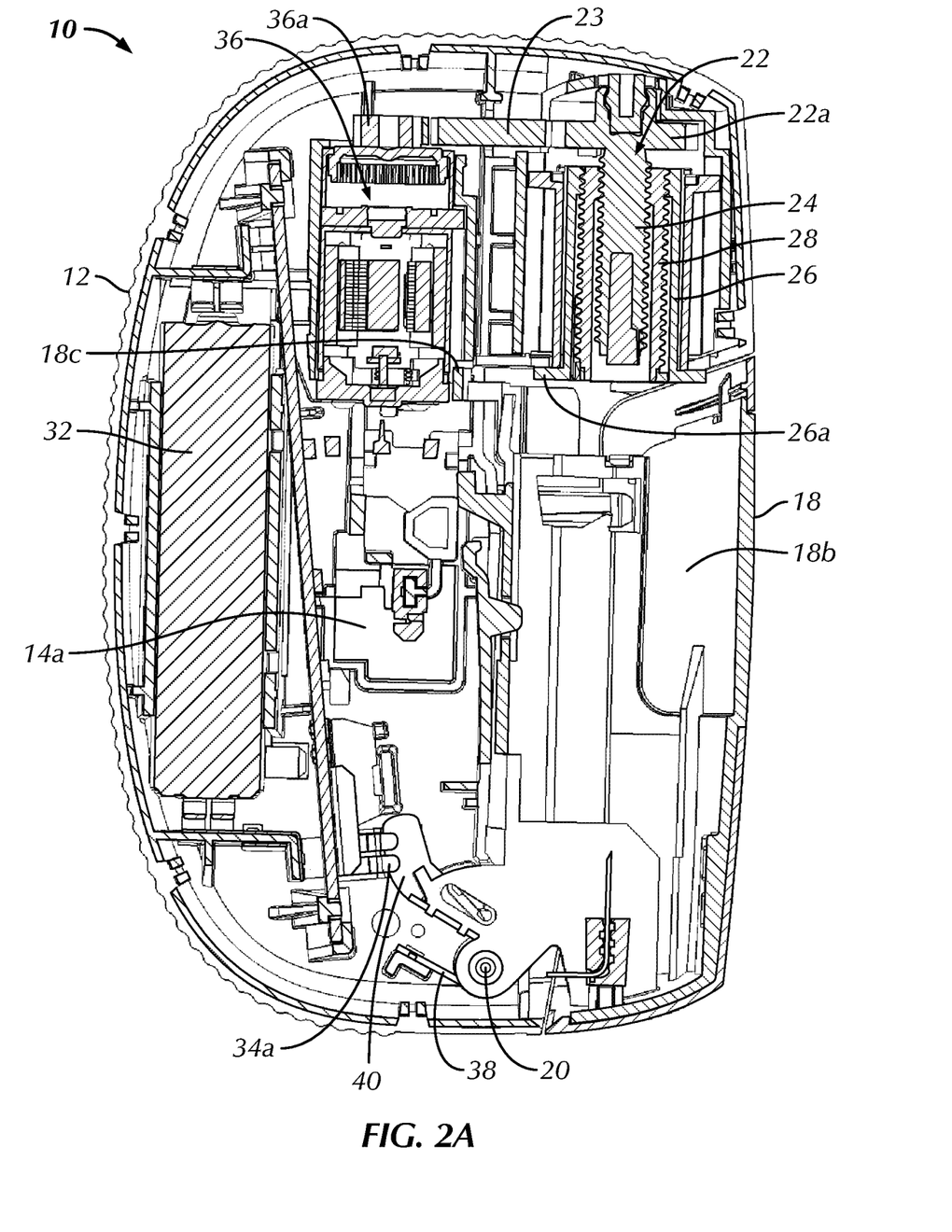
FIG. 2A is a cross-sectional view of the injector of FIG. 1, taken along the sectional line 2-2 of FIG. 1, with a cartridge door of the injector positioned in a fully closed position thereof.
Figure 2B:
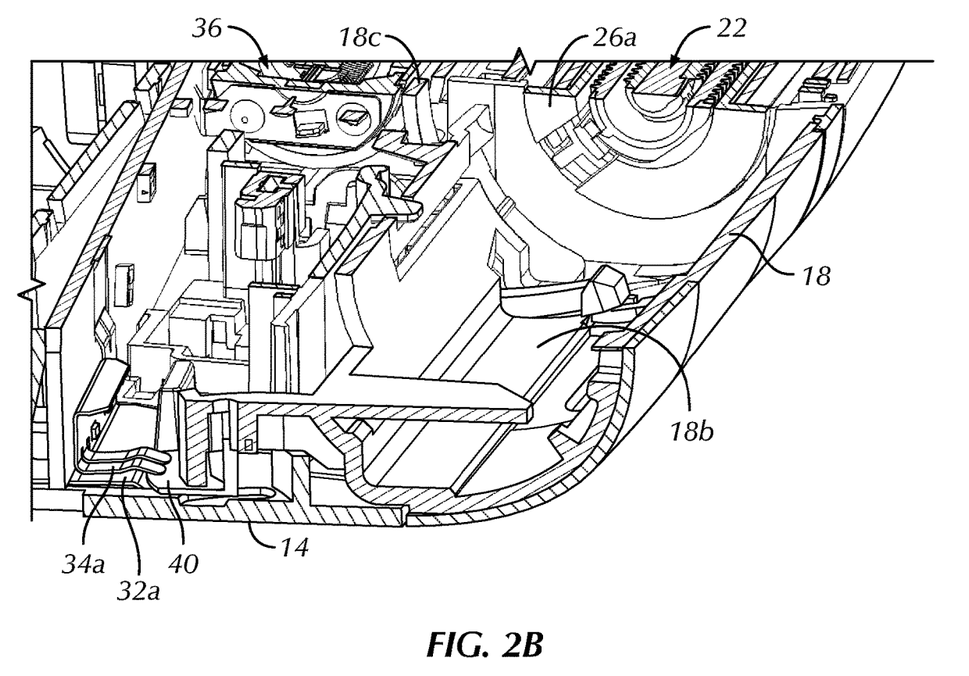
FIG. 2B is a partial perspective view of the cross-sectional view of FIG. 2A.
Figure 3:
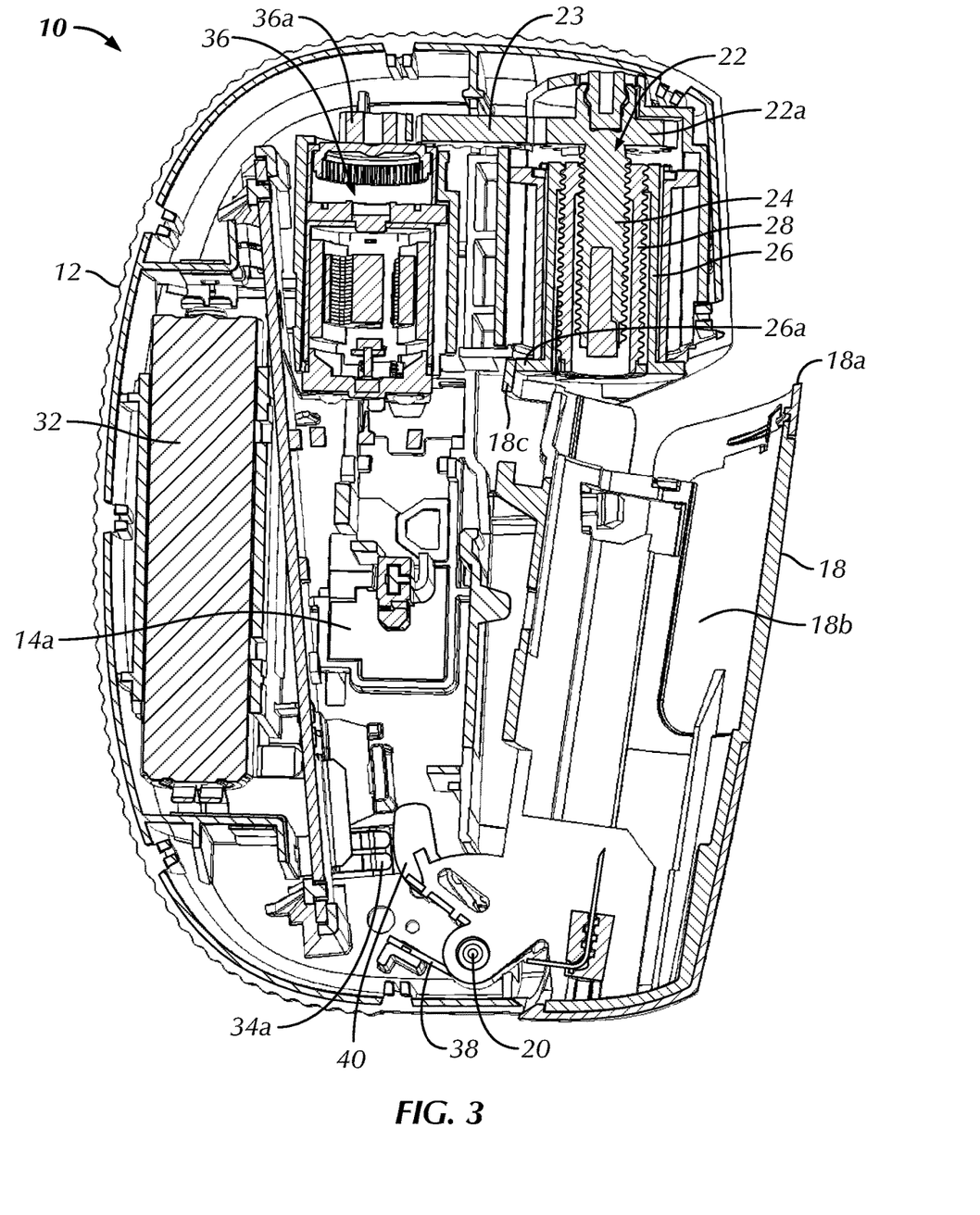
FIG. 3 is a cross-sectional view of the injector of FIG. 1, taken along the sectional line 2-2 of FIG. 1, with the cartridge door positioned in a partially closed position thereof and a movable locking member extending into a pathway of the cartridge door.

The arm 40 is configured, i.e., shaped, dimensioned, angled, or a combination thereof, to be positioned in the first state thereof in the fully closed initial position of the cartridge door 18 (FIGS. 2A, 2B). The arm 40 is also configured to move to the second state thereof (FIGS. 3, 4) with movement of the cartridge door 18 out of the fully closed position thereof to the open position thereof. In the illustrated embodiment, as shown in FIG. 3, the arm 40 is configured to be positioned in the second state thereof in the partially closed position of the cartridge door 18 when the cartridge door 18 is blocked by the driving assembly 22 prior to achievement of a "pass" outcome by the self-test.

As should be understood by those of ordinary skill in the art, the electrically insulated member 40 may alternatively be attached to other movable components of the injector 10 or separately and movably mounted to the injector housing 12 in a manner permitting the arm 40 to perform the functions thereof described herein. For example, without limitation, the electrically insulated member 40 may take the form of a conventional user-removable battery isolator or the electrically insulated member 40 may be employed in the injector 10 as described in U.S. Patent Application Publication No. 2013/0310753, entitled, "Method For Selectively Powering A Battery-Operated Drug-Delivery Device and Device Therefor," the entire contents of which are incorporated by reference herein. As also should be understood, the electrically insulated member 40 may be interposed between a direct contact of the power supply 32 and an opposing contact of the power supply circuit 34, in the first state thereof, or, alternatively, the electrically insulated member 40 may be interposed between opposing contacts formed elsewhere along the power supply circuit 34, in the first state thereof.

In use, the injector 10 may be initially delivered to a user with the cartridge door 18 in the fully closed position thereof. For example, where a biasing member 38 is employed to bias the cartridge door 18 into the open position, the injector packaging 50 may maintain the cartridge door 18 in the fully closed position thereof (FIG. 1), against the force of the biasing member 38. As should be understood, however, the cartridge door 18 may be positioned in the fully closed position thereof via other mechanisms currently known or that later become known. As one example, a removable liner (not shown) may be positioned over a portion of the cartridge door 18 and the injector housing 12 to maintain the door 18 in the closed position. Alternatively, the cartridge door 18 may be locked, e.g., in the fully closed position (with or without the presence of the biasing member 38).

Where an electrically insulated member 40 is employed in the injector 10, initially interposed between the at least one contact 32a of the power supply 32 and the respective at least one opposing contact 34a of the power supply circuit 34, the power supply 32 is initially electrically disconnected to avoid drainage thereof. A user may manually withdraw and remove the electrically insulated member 40 from between the at least one contact 32a of the power supply 32 and the respective at least one opposing contact 34a of the power supply circuit 34 to power on the controller 30 and initiate the self-test.

Where the cartridge door 18 is biased to the open position thereof, e.g., via the biasing member 38, removal of the injector 10 from the packaging 50 thereof will enable the biasing member 38 to move out of the fully closed position thereof toward the open position thereof, only to be blocked by the driving assembly 22 in a partially closed position (FIG. 3). Alternatively, where the cartridge door 18 is not biased to the open position thereof, a user may manually move the cartridge door 18 from the fully closed position thereof to the partially closed position thereof. Where the electrically insulated member 40 is coupled to the cartridge door 18, the electrically insulated member 40 may be removed from between the at least one contact 32a of the power supply 32 and the respective at least one opposing contact 34a of the power supply circuit 34 (to reach the second state of the member 40) during movement of the cartridge door 18 from the fully closed position to the partially closed position, powering on the controller 30 to automatically initiate the self-test. The cartridge door 18 is blocked from reaching the fully open position thereof because of the extension of the driving assembly 22 (or other movable locking mechanism) into the cartridge door 18 pathway, as previously explained. Alternatively, where an electrically insulated member 40 is not employed, a user may power the device on via an activation switch (not shown) or via a remote mobile device (not shown) connected, e.g., paired, with the injector 10, to initiate the self-test.

If the self-test yields a "fail" outcome, the cartridge door 18 remains locked in the at least partially closed position thereof, preventing the cartridge 60 from being inserted into the injector 10, and a failure indicator may be activated. For example, an audible tone and/or visual indicator, a combination thereof or the like, indicating failure, may be activated. A user may then obtain another injector 10 and salvage the cartridge 60 for use with the newly obtained injector 10, rather determining failure of the injector 10 after inserting and unsealing of the cartridge 60, and, thereafter, requiring both a new injector 10 and a new cartridge 60.

Otherwise, if the self-test yields a "pass" outcome, the controller 30 directs the actuator 36 to withdraw the driving assembly 22 out of the pathway of the cartridge door 18 (as previously explained), unlocking the cartridge door 18 and enabling the cartridge door 18 to be moved into the fully open position thereof. For example, where the biasing member 38 is employed, the cartridge door 18 will be automatically moved to the fully open position thereof under the force of the biasing member 38 upon passing of the self-test, as withdrawal of the driving assembly 22 from the pathway of the cartridge door 18 will uninhibit the biasing member 38. Alternatively, where the biasing member 38 is not employed, a user may manually move the cartridge door 18 into the fully open position thereof after the driving assembly 22 is withdrawn out of the pathway of the cartridge door 18. Yet further, the biasing member 38 may move the cartridge door 18 to a partially open state and the user may finish moving the cartridge door 18 to the fully open state thereof. An audible and/or visual indicator, a combination thereof or the like may inform the user that the self-test has achieved a "pass" outcome and that the cartridge door 18 has been unlocked.

In the fully open position of the cartridge door 18, the cartridge 60 may be inserted into the interior channel 18b (FIG. 4), and, thereafter, the cartridge door 18 may be moved back into the fully closed position thereof, axially aligning the cartridge 60 with the driving assembly 22. The controller 30 may then direct the actuator 36 to extend the driving assembly 22 into the interior channel 18b of the cartridge door 18 to engage the cartridge 60, fluidly connect the cartridge 60 with the injection needle (not shown) and expel the substance from the cartridge 60 and out of the injector 10 through the injection needle, in a manner well understood by those of ordinary skill in the art.

It will be appreciated by those skilled in the art that changes could be made to the embodiments described above without departing from the broad inventive concept thereof. For example, without limitation, the self-test may include a secondary device, e.g., a mobile device, pair with the injector 10 to perform some or all of the functions performed by the controller 30 with respect to the self-test. The mobile device may also perform other or additional functions, such as verifying the user and/or the cartridge 60 (e.g., by scanning a barcode). It is understood, therefore, that this invention is not limited to the particular embodiments disclosed, but it is intended to cover modifications within the spirit and scope of the present invention, as set forth in the appended claims.

We claim:

1. An injector configured to receive a cartridge containing a substance to be dispensed, the injector comprising:
   an injector housing;
   an injector door movably mounted to the injector housing between a closed position and an open position, the injector door being initially locked preventing the injector from receiving the cartridge; and
   a controller configured to conduct a self-test on operability of at least one component of the injector upon activation of the injector, the self-test having a pass or fail outcome,
   wherein the injector door is unlocked, such that the injector is configured to receive the cartridge solely upon achievement of the pass outcome.

2. The injector of claim 1, further comprising a movable locking mechanism protruding into a pathway of the injector door from the closed position to the open position and blocking the injector door from reaching the open position, the movable locking mechanism being configured to be withdrawn from the pathway of the injector door upon achievement of the pass outcome.

3. The injector of claim 1, further comprising:
   a driving assembly configured to engage the cartridge and expel the substance therefrom upon of the cartridge being received into the injector, the driving assembly being movable between a retracted configuration and an extended configuration,
   wherein the driving assembly is initially oriented in a partially extended configuration protruding into a pathway of the injector door blocking the injector door from moving to the open position prior to achievement of the pass outcome, and the driving assembly is retracted into the retracted configuration upon achievement of the pass outcome, withdrawing the driving assembly from the pathway of the injector door.

4. The injector of claim 1, wherein the injector door comprises a cartridge door having an open end and an interior channel to receive the cartridge, the open end is sufficiently obscured by the injector housing to prevent the injector from receiving the cartridge into the interior channel when initially locked, and the open end is sufficiently exposed to receive the cartridge into the interior channel in the open position.

5. The injector of claim 4, further comprising:
   a driving assembly configured to engage the cartridge and expel the substance therefrom upon the cartridge being received into the interior channel and the injector door being in the closed position,
   wherein the driving assembly is movable between a retracted configuration and an extended configuration, and
   wherein the driving assembly is oriented in a partially extended configuration prior to achievement of the pass outcome, protruding into the interior channel thereby blocking the cartridge door from moving into the open position, and the driving assembly is retracted into the retracted configuration upon achievement of the pass outcome.

6. The injector of claim 4, further comprising a biasing member configured to bias the cartridge door toward the open position.

7. The injector of claim 1, further comprising:
   a power supply;
   a power supply circuit electrically connecting the power supply with the controller; and
   an electrically insulated member,
   wherein the electrically insulated member is movable from a first state to a second state, the electrically insulated member is interposed between contact of the power supply and an opposing contact of the power supply circuit in the first state, thereby disconnecting the power supply from the power supply circuit, and the electrically insulated member is removed from between the contact of the power supply and the opposing contact of the power supply circuit in the second state, thereby connecting the power supply with the power supply circuit and providing power to the controller.

8. The injector of claim 7, wherein the electrically insulated member comprises an arm coupled to the injector door, the electrically insulated member is initially positioned in the first state when the injector door is in the closed position, and the electrically insulated member is moved to the second state upon movement of the injector door out of the closed position.

9. The injector of claim 7, wherein the electrically insulated member is moved from the first state to the second state during movement of the injector door from the closed position to an at least partially closed position.

10. The injector of claim 1, wherein the injector is activated by an activation switch.

11. The injector of claim 1, wherein the injector is activated by powering on the injector.

12. The injector of claim 11, wherein the injector is powered on via a remote mobile device.

13. The injector of claim 1, further comprising a biasing member configured to move the injector door towards the open position when the injector is removed from a packaging.

14. The injector of claim 1, wherein the self-test includes a sensor detecting motion of a moveable component of the injector.

15. The injector of claim 1, wherein the injector door is initially locked in an at least partially closed position.

16. A method of operation of an injector configured to receive a cartridge containing a substance to be dispensed, the method comprising:
   conducting, with a controller of the injector, a self-test on operability of at least one injector component upon activation of the injector, the self-test having a pass or fail outcome; and
   unlocking an injector door to enable the injector to receive the cartridge solely upon achievement of the pass outcome, the injector door being movably mounted to a housing of the injector between a closed position and an open position, the injector door being previously locked preventing the injector from receiving the cartridge.

17. The method of claim 16, wherein the unlocking comprises withdrawing a locking mechanism from protruding into a pathway of the injector door from the closed position to the open position, the locking mechanism previously blocking the injector door from reaching the open position.

18. The method of claim 16, wherein the unlocking comprises withdrawing a driving assembly, movable between a retracted configuration and an extended configuration and configured to engage the cartridge and expel the substance therefrom upon the cartridge being received into the injector, out of a partially extended configuration of the driving assembly, protruding into a pathway of the injector door from the closed position to the open position, and into the retracted configuration of the driving assembly.

19. The method of claim 16,
   wherein the injector door comprises a cartridge door and a driving assembly,
   wherein the cartridge door has an open end and an interior channel to receive the cartridge, the open end is sufficiently obscured by the injector housing in the closed position to prevent the injector from receiving the cartridge into the interior channel, and the open end is sufficiently exposed in the open position to receive the cartridge into the interior channel,
   wherein the driving assembly is movable between a retracted configuration and an extended configuration, and the driving assembly is configured to engage the cartridge and expel the substance therefrom upon the cartridge being received in the injector, and
   wherein the unlocking comprises withdrawing the driving assembly out of a partially extended configuration of the driving assembly, protruding into the interior channel of the cartridge door, and into the retracted configuration of the driving assembly, withdrawn from the interior channel.

20. The method of claim 16, wherein the injector further comprises a power supply, a power supply circuit electrically connecting the power supply with the controller, and an electrically insulated member, the method further comprising:
   moving the electrically insulated member from a first state to a second state, the electrically insulated member is interposed between contact of the power supply and an opposing contact of the power supply circuit in the first state, thereby disconnecting the power supply from the power supply circuit, and the electrically insulated member is removed from between the contact of the power supply and the opposing contact of the power supply circuit in the second state, thereby connecting the power supply with the power supply circuit and providing power to the controller.

21. The method of claim 20, wherein the electrically insulated member comprises an arm coupled to the injector door, and moving the electrically insulated member from the first state to the second state comprises moving the injector door out of the closed position.

22. An injector configured to receive a cartridge containing a substance to be dispensed, the injector comprising:
   an injector housing;
   an injector door movably mounted to the injector housing between a closed position and an open position, the injector door being initially locked preventing the injector from receiving the cartridge;
   a controller configured to conduct a self-test on operability of at least one component of the injector upon activation of the injector, the self-test having a pass or fail outcome; and
   a driving assembly configured to engage the cartridge and expel the substance upon the cartridge being received in the injector, the driving assembly being movable between a retracted configuration and an extended configuration, wherein the driving assembly is initially oriented to protrude into a pathway of the injector door to lock the injector door prior to achievement of the pass outcome,
   wherein the driving assembly is retracted upon achievement of the pass outcome, thereby withdrawing the driving assembly from the pathway of the injector door to unlock the injector door enabling the cartridge to be received in the injector, solely upon achievement of the pass outcome.

23. The injector of claim 22, wherein the injector door is initially locked in an at least partially closed position.

24. The injector of claim 22, wherein the driving assembly is initially oriented in a partially extended configuration to protrude into the pathway of the injector door and lock the injector door.

25. The injector of claim 22, wherein the self-test includes a sensor detecting motion of a moveable component of the injector.

26. The injector of claim 22, further comprising a biasing member configured to bias the injector door toward the open position.

27. An injector configured to receive a cartridge containing a substance to be dispensed, the injector comprising:
   an injector housing;
   an injector door movably mounted to the injector housing between a closed position and an open position, the injector door being initially locked preventing the injector from receiving the cartridge;
   a controller configured to conduct a self-test on operability of at least one component of the injector upon activation of the injector, the self-test having a pass or fail outcome;
   a power supply;
   a power supply circuit electrically connecting the power supply with the controller; and
   an electrically insulated member comprising an arm coupled to the injector door,
   wherein the electrically insulated member is initially positioned in a first state when the injector door is in the closed position, and the electrically insulated member is interposed between a contact of the power supply and an opposing contact of the power supply circuit in the first state, thereby disconnecting the power supply from the power supply circuit, wherein the electrically insulated member is moved to a second state upon movement of the injector door out of the closed position, and the electrically insulated member is removed from between the contact of the power supply and the opposing contact of the power supply circuit in the second state, thereby connecting the power supply with the power supply circuit and providing power to the controller, and wherein the injector door is unlocked enabling the cartridge to be received into the injector, solely upon achievement of the pass outcome.

28. The injector of claim 27, wherein the injector door is fully closed when in the closed position, and the injector door is in an at least partially closed position when the electrically insulated member is in the second state.

29. The injector of claim 27, wherein the arm is integrally formed with the injector door.

30. The injector of claim 27, further comprising a biasing member configured to bias the injector door toward the open position.

* * * * *